United States Patent [19]

Hotchkiss et al.

[11] Patent Number: 5,096,811
[45] Date of Patent: Mar. 17, 1992

[54] NOVEL ASSAY SYSTEM FOR MEASUIRNG HUMAN PLASMINOGEN ACTUATOR ACTIVITY

[75] Inventors: Adair J. Hotchkiss, Half Moon Bay; Marjorie A. Mohler, Oakland, both of Calif.

[73] Assignee: Genentech, Inc., South San Francisco, Calif.

[21] Appl. No.: 432,924

[22] Filed: Nov. 7, 1989

Related U.S. Application Data

[63] Continuation of Ser. No. 840,127, Mar. 12, 1986, abandoned.

[51] Int. Cl.[5] .......................... C12Q 1/56; C12Q 1/38; G01N 33/86
[52] U.S. Cl. ........................................ 435/13; 435/7.4; 435/7.6; 435/7.71; 435/23; 435/24; 435/184; 435/212; 435/217; 436/69; 424/94.64
[58] Field of Search ................. 435/13, 23, 7, 24, 212, 435/217, 184; 436/69; 424/94.64

[56] References Cited

U.S. PATENT DOCUMENTS 4,029,694 12/1986 Harpel ................ 435/13 X
4,318,904 9/1982 Shaw et al. .......... 435/13 X
4,563,420 1/1986 Verheijen et al. .......... 435/13

OTHER PUBLICATIONS

Chemical Abstract 100 (15) 116863, "Quantitation of Tissue-Type Plasminigen Activator . . . by Use of an Enzyme Immunoassay", Rijken et al., *Thromb. Res.*, 33(2), 145–53, 1984.

Chemical Abstract 102(1)2611, "Quantitative Determination of Tissue-Type Plasminogen Activator", Kyowa Co., Ltd., Jpn. KOKAI TOKKYO KOHO, JP 59174759 A2, Oct. 3, 1984.

Lijnen et al., "Inhibition of Trypsin-Like Serine Proteinases by Tripeptide Arginyl and Lysyl Chloromethylketones", *Thrombosis Research* 34; 431–437 (1984).

Kettner, Charles and Shaw, Elliott, Brief Communication, "D-PHE-PRO-ARGCH$_2$Cl-A Selective Affinity Label for Thrombin", *Thrombosis Research* 14; 969–973 (1979).

Korninger, C., Stassen, J. M. and Collen, D., "Turnover of Human Extrinsic (Tissue-Type) Plasminogen Activator in Rabbits", *Thromb. Haemostas*, (Stuttgart) 46(3) 658–661 (1981).

Primary Examiner—Esther L. Kepplinger
Assistant Examiner—Carol A. Spiegel
Attorney, Agent, or Firm—Walter H. Dreger

[57] ABSTRACT

Disclosed is a means useful for selectively inhibiting human tissue plasminogen activator utilizing a thrombin inhibitor, illustrated by D-Phe-Pro-Arg-chloromethyl ketone (PPACK), thus providing a novel assay system for measuring human tissue plasminogen activator activity.

3 Claims, 5 Drawing Sheets

NOVEL ASSAY SYSTEM FOR MEASUIRNG HUMAN PLASMINOGEN ACTUATOR ACTIVITY

This application is a continuation of application Ser. No. 840,127, filed Mar. 12, 1986, now abandon.

FIELD OF THE INVENTION

This invention is directed to a novel assay system making possible the monitoring of thrombolytic events without interference by various interacting protein artifacts. In particular, the present assay system permits the accurate measurement in vitro of levels of human tissue-type plasminogen activator in the presence of various plasma coagulation and fibrinolytic components.

Numerical reference is made parenthetically herein to various documents that are listed in corresponding numerical order in the appended Bibliography which forms a part of the present specification. These documents are hereby incorporated by reference.

BACKGROUND OF THE INVENTION

Human tissue-type plasminogen activator is a thrombolytic agent that activates plasminogen to plasmin at the site of a fibrin clot (1,2,3). Plasmin is subsequently responsible for the proteolytic degradation of fibrin; thus, human tissue-type plasminogen activator mediates the dissolution of blood clots and is consequently useful in the treatment of various thrombotic disorders.

When human tissue-type plasminogen activator is used in thrombolytic therapy, monitoring a number of plasma components can be useful to evaluate the modifications in the coagulation and fibrinolytic systems. These components included fibrinogen, fibrin(ogen) degradation products (FDPs), plasminogen, alpha-2-antiplasmin and immunoreactive human tissue-type plasminogen activator. In order to measure circulating amounts of these components, as well as human tissue-type plasminogen activator, as indicia important to determine an effective therapeutic dose of human tissue-type plasminogen activator, blood samples are drawn prior to and during human tissue-type plasminogen activator administration. In such blood samples, human tissue-type plasminogen activator may continue to activate plasminogen to plasmin in vitro, which in turn can lead to in vitro consumption of fibrinogen, plasminogen, alpha-2-antiplasmin, and the production of FDPs resulting from the proteolysis of fibrinogen by plasmin.

Free human tissue-type plasminogen activator forms complexes with protease inhibitors such as alpha-2-antiplasmin, alpha-1-antitrypsin, alpha-2-macroglobulin, Cl-esterase inhibitor and human tissue-type plasminogen activator fast acting inhibitor (4–7). These complexes might alter the immunoreactivity of human tissue-type plasminogen activator in various degrees, which could cause inaccurate measurement of its concentration in plasma.

To accurately determine fibrinolytic changes in vivo, subsequent proteolytic events by plasmin must be minimized in vitro. It was perceived that the most direct method for minimizing or eliminating these proteolytic events (artifacts) would be to selectively neutralize the proteolytic activity of human tissue-type plasminogen activator. This could be accomplished by the rapid introduction of an irreversible protease inhibitor. Several such inhibitors include various peptide chloromethyl ketones (8,9).

Therefore, it is an object of the present invention to identify, prepare and use during plasma collection a rapidly acting, soluble inhibitor of human tissue-type plasminogen activator that does not interfere in an assay monitoring the total fibrinolytic system.

SUMMARY OF THE INVENTION

Now it has been discovered that a potent thrombin inhibitor rapidly and selectively inhibits human tissue-type plasminogen activator interfering neither with accurate measurement of its levels nor with the accurate measurement of levels of other plasma components. The determination of its surprising selective activity with respect to human tissue-type plasminogen activator in thromobolytic/coagulation assays is the basis of the present invention.

The active inhibitor component of this invention is identified as a tripeptide chloromethyl ketone, namely, D-Phe-ProArg-Chloromethyl Ketone (PPACK). This invention relates to the use of PPACK in blood samples in amounts sufficient to inhibit human tissue-type plasminogen activator to an immunoreactive, functionally inactive form without concomitant interference with other plasma coagulation/fibrinolytic components such that levels of human tissue-type plasminogen activator and such other plasma components are susceptible to accurate in vitro measurement relating back to the in vivo thrombolytic status at the time the blood sample is drawn. The present invention is directed to such use of PPACK and to all associated embodiments.

A single blood sample collected with a conventional protease inhibitor such as aprotinin cannot be used for accurate simultaneous measurement of plasminogen, alpha-2-antiplasmin, fibrinogen by a thrombin time method, fibrinogen by salt precipitation, FDPs and immunoreactive human tissue-type plasminogen activator. This invention is based on use of PPACK as an effective protease inhibitor which will allow accurate, thrombolytically stable measurement of all of these parameters in a single blood sample.

It is further contemplated that other peptide chloromethyl ketones could function equivalently to PPACK and therefore enjoy similar selective inhibition of human tissue-type plasminogen activator. Such equivalents include Dansyl-Glu-Gly-Arg-Chloromethyl Ketone, D-Val-Gly-Arg-Chloromethyl Ketone, D-Ile-Pro-Arg-Chloromethyl Ketone (see 8,9) and $X_{(n)}$-Arg-Chloromethyl Ketone, where X is any amino acid and n is from about 1 to 10.

DETAILED DESCRIPTION

Aprotinin, a known plasmin inhibitor, interferes with the measurement of plasminogen and alpha-2-antiplasmin since these assays depend on the activity of plasmin. PPACK, although a weak plasmin inhibitor (10), seems not to block the potential active site of the proenzyme plasminogen since plasminogen levels are not altered in the presence of PPACK. Similarly, there is no change in the level of the plasmin inhibitor, alpha-2 antiplasmin, in normal plasma collected in the presence of PPACK. Although PPACK is an inhibitor of plasmin, the reaction may either be too slow or the residual PPACK levels may be too low to inhibit the plasmin which is added to the alpha-2-antiplasmin assay. Aprotinin was also found to be minimally effective in inhibiting plasmin generated FDPs in contrast to PPACK which selectively inactivates human tissue-type plasminogen activator, the source of the activation of plasminogen.

Figure 2:
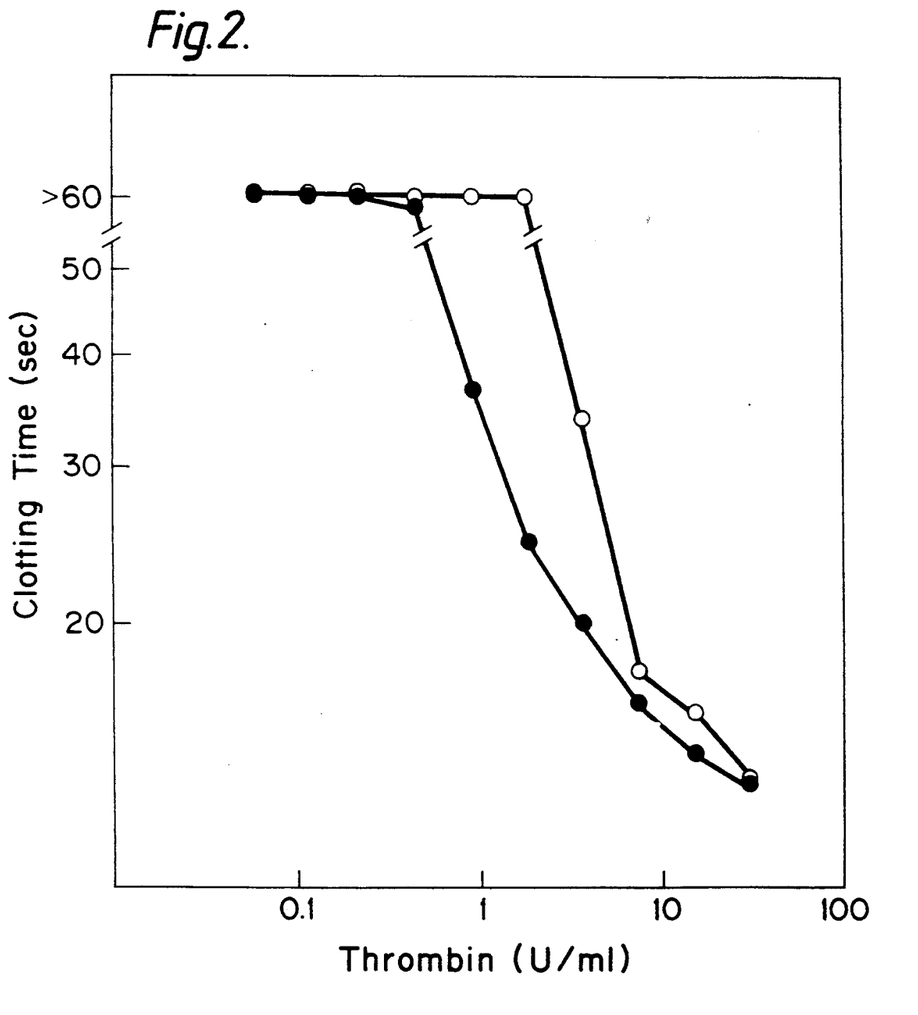
FIG. 2 shows thrombin clotting times for normal human plasma with (o) and without (•) PPACK (1 $\mu$M).
Figure 3:
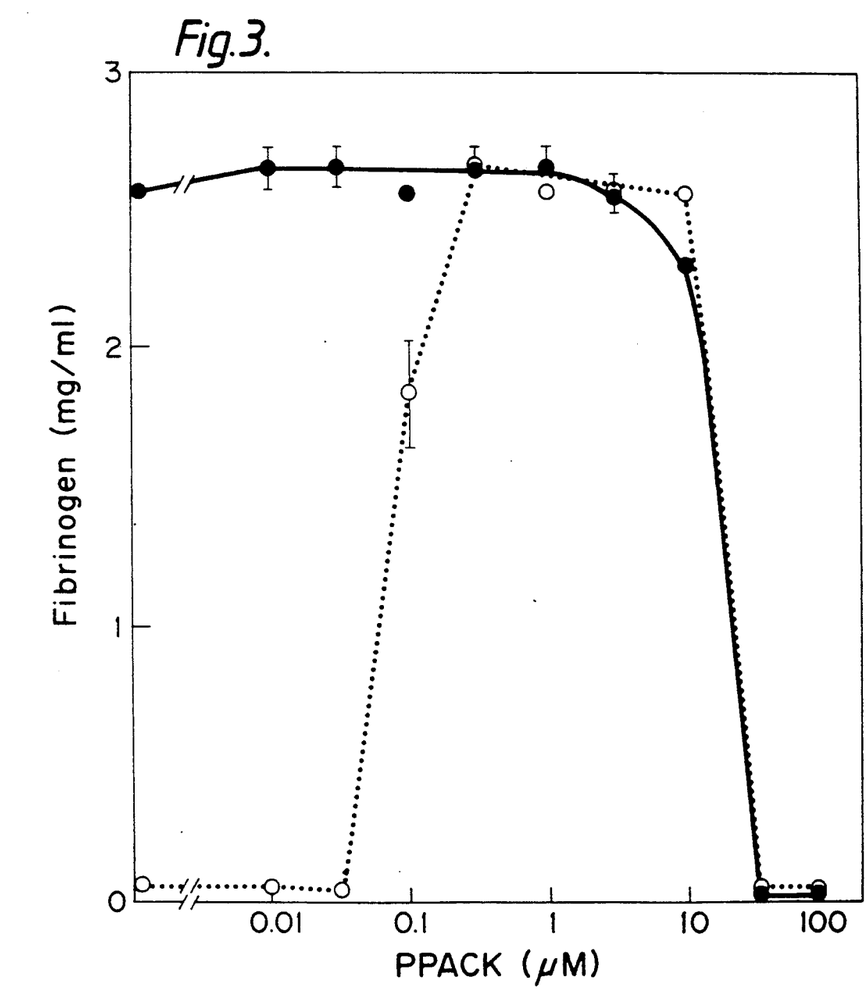
FIG. 3 shows the effect of PPACK (1 $\mu$M) on apparent fibrinogen levels by the modified Clauss method with (o) and without (•) 5 $\mu$g/ml human tissue-type plasminogen activator. Error bars (mean±s.e.m.) are omitted when the error is smaller than the symbol.

The concentration of PPACK which is effective for samples with pharmacological levels of human tissue-type plasminogen activator is from about 0.1 to about 10 µM, preferably from about 0.3 to about 5 µM. Since PPACK is a thrombin inhibitor, excess thrombin must be used in thrombin dependent assays which quantitate fibrinogen (FIG. 2). At PPACK concentration above 10 µM major underestimations of fibrinogen may result (FIG. 3).

The in vitro formation of SDS stable human tissue-type plasminogen activator protease inhibitor complexes, especially the fast acting endothelial type of platelet type inhibitor (11), has serious consequences for accurate determination of the role of plasma protease inhibitors in the metabolism of human tissue-type plasminogen activator as well as the quantitation of immunoreactive human tissue-type plasminogen activator. The speed at which these complexes form in vitro (12,13) necessitates rapid mixing of the blood with PPACK since any platelet activation may increase the concentration of platelet derived fast acting inhibitor. The concentration of immunoreactive human tissue-type plasminogen activator apparently decreases in the presence of aprotinin (FIG. 5); this is probably due to the formation of protease inhibitor complexes which have altered immunoreactivity although the extent of change in immunoreactivity may depend on the specific antibodies used for the assay.

A. MATERIALS AND METHODS

1. Human Tissue-type Plasminogen Activator Activity in Plasma Containing PPACK Recombinant human tissue-type plasminogen activator at 5 µg/ml was added to 4.6 mM dipotassium ethylenediamine tetraacetic acid ($K_2EDTA$) plasma containing 0-100 µM PPACK (Calbiochem, La Jolla, CA) and incubated for 1 hr. at 2-8 degrees C., frozen then thawed at 37 degrees C. All PPACK solutions were prepared in 10 mM HCl. Twenty microliter aliquots of plasma were then assayed for residual human tissue-type plasminogen activator activity by an amidolytic method (14) with synthetic substrate S-2288 (Kabi Diagnostics). Amidolytic activity was spectrophotometrically determined as change in optical density at 2.5 hours of incubation.

2. Fibrinogen

Fibrinogen was assayed by either a sodium sulfite precipitation method (15) or by a modification (16) of the Clauss thrombin dependent assay (17). The thrombin dependent assay was performed as follows: Twenty microliters of plasma, incubated at 37 degrees C. for 15 minutes, was added to 180 µl of Owens veronal buffer and incubated for 5 minutes at 37 degrees C. When EDTA was used as the anticoagulant, additional calcium, 10 mM, was included in the veronal buffer. A small stirring rod was added to the tube, 100 µl of thrombin (Warner-Lambert Co., Morris Plains, N.J.) was added and the contents were stirred gently with an upward motion against the test tube wall. Time to clot was determined when the first sign of a clot was detected. The concentration of thrombin was predetermined to be that which caused clotting of normal plasma in 12 seconds; thrombin was between 30 to 40 U/m in the final mixture. Fibrinogen was considered to be zero when the clotting time was greater than 60 seconds.

3. Inhibition of Thrombin with PPACK

Whole blood was added to tubes containing EDTA as an anticoagulant, 4.6 mM final concentration, and 1 µM PPACK was then added to half of the tubes. The samples were kept at 4 degrees C. for 30 minutes before plasma was prepared. The samples were centrifuged at 10,000 x g for 5 minutes at 4 degrees C. and plasma collected. Clotting time was determined as described in the fibrinogen assay procedure with thrombin concentrations of 0.06 units/ml to 30 units/ml.

4. PPACK Interference in the Modified Clauss Fibrinogen Assay

The interaction of PPACK with the thrombin dependent fibrinogen assay was examined over a range of PPACK concentrations. Whole blood was added to tubes which were prepared as follows: citric acid was titrated to pH 4.4 with NaOH and aliquoted with various concentrations of PPACK to individual sample tubes; the PPACK/citrate tubes were lyophilized such that when 1.0 ml of whole blood was added the citrate concentration was 24 mM and PPACK was 0-30 µM. Although this concentration of citrate caused some hemolysis, the hemolysis can be avoided by using a final concentration of 10 mM citrate. Human tissue-type plasminogen activator at a concentration of 5 µg/ml was added to half of the tubes containing whole blood. Plasma was prepared as described above and assayed for fibrinogen.

5. Formation of $^{125}I$ Human Tissue-type Plasminogen Activator Complexes

A human tissue-type plasminogen activator sample containing 150 µg protein was labeled with 2.5 mCi of carrier free $^{125}$Iodine in the presence of one iodobead (Pierce, Rockford, IL) for 15 min. at room temperature. Unincorporated label was separated from labeled human tissue-type plasminogen activator by cross-linked dextran bead (SEPHADEX G-25) chromatography using a PD-10 disposable column (Pharmacia, Upsala, Sweden). This human tissue-type plasminogen activator preparation resulted in a specific activity of 4 µCi/µg protein. A preparation of human tissue-type plasminogen activator labeled similarly with $Na^{127}I$ retained full enzymatic activity as measured by the in vitro clot lysis assay as previously described (18).

EDTA was added to human and rabbit whole blood collected by careful venipuncture and PPACK was added at 0, 0.05, and 5.0 μM. Human tissue-type plasminogen activator was then added to a final concentration of 5 μg/ml with a trace quantity of $^{125}I$ human tissue-type plasminogen activator and the whole blood was incubated for 2 hr. at 4 degrees C. before plasma was prepared. Samples were prepared for electrophoresis by adding 90 μl of 20 mM tris, 5 percent sodium dodecyl sulfate (SDS), pH 6.8 to 10 μl of the plasma and heating at 95 degrees C. for 5 minutes.

The equivalent of one microliter of plasma was loaded on 10 percent polyacrylamide gels as described by Laemmli (19) using 0.75 mm gels. Gels were dried on membrane backing (Bio-Rad, Richmond, CA) and exposed to Kodak X-90at-AR film at −70 degrees C. Molecular weight markers were from Pharmacia and the molecular weight of the human tissue-type plasminogen activator inhibitor complex was determined by extrapolating the molecular weight from a mobility plot.

6. In Vitro Activation of Plasminogen to Plasmin by Human Tissue-type Plasminogen Activator Human and rabbit whole blood was collected by venipuncture and EDTA was added at a final concentration of 4.6 mM to inhibit coagulation. Whole blood was immediately placed on ice and the protease inhibitor PPACK was added at various concentrations with or without aprotinin 150 KIU/ml (Sigma, St. Louis, MO); human tissue-type plasminogen activator was added to a final concentration of 5 μg/ml. After 1 hour at 4 degrees C. the whole blood was centrifuged for 10 minutes at 10,000 xg in a Beckman microfuge at 4 degrees C. Plasma was removed and immediately frozen at −70 degrees C. Plasma samples were thawed for 15 minutes at 37 degrees C. in a warm room and were assayed for fibrinogen, FDP, plasminogen, alpha-2-antiplasmin.

7. Fibrinogen-degradation Products

Fibrinogen-degradation products were assayed by ELISA using monoclonal antibody specific for Bbeta (1–42), a specific plasmin cleavage fragment from fibrinogen or Fibrin I (20).

8. Plasminogen

Plasminogen was assayed by an amidolytic method with the synthetic substrate S-2251 (Kabi Diagnostics, Stockholm, Sweden) (21,22) after a 10 minute pre-incubation with urokinase (Sigma, St. Louis, MO) at a concentration of 333 U/ml. The plasmin inhibitors in the plasma sample were first neutralized by acidification (23). Results were expressed as a percentage of normal values by comparison with values from a standard curve prepared from reference human plasma (Dade, Aguada, P.R.).

9. Alpha-2-Antiplasmin

Alpha-2-antiplasmin activity was assayed by an amidolytic method (24) with the synthetic substrate S-2251. Results were expressed as percentage of normal values by comparison with values from a standard curve prepared from reference plasma.

10. Administration of human tissue-type plasminogen activator to Rhesus Monkeys Adult rhesus monkeys were lightly anesthetized with Ketamine and a 3 cm catheter was placed in a femoral vein. The catheter was flushed with 0.15M NaCl containing 3 U/ml heparin. The human tissue-type plasminogen activator was infused at a rate of 50 μg/kg/min for 60 minutes. Two independent blood samples were collected by venipuncture at 55 minutes and 4 hours. One sample was taken with aprotinin in the syringe, 200 KIU/ml final concentration. The second sample was taken with 50 μl of 20 μM PPACK per ml of whole blood. Both blood ampules were added to tubes containing EDTA, 4.6 mM final, and the plasma was prepared as described above. Immunoreactive human tissue-type plasminogen activator was measured by an ELISA procedure utilizing a rabbit polyclonal antibody.

B. EXAMPLES

Figure 1:
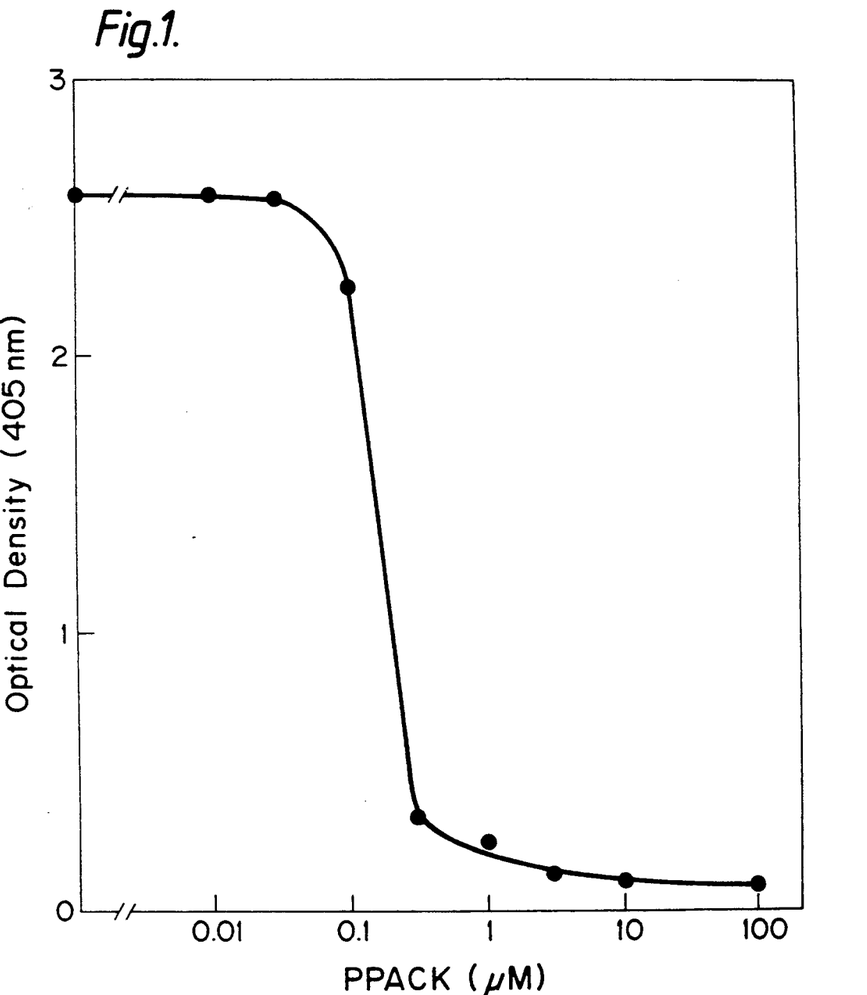
FIG. 1 shows the inhibition of human tissue-type plasminogen activator amidolytic activity in plasma using the S-2288 chromogenic substrate.

1. Inhibition of the Amidolytic Activity of Human Tissue-type Plasminogen Activator The most direct way to measure the inhibition of human tissue-type plasminogen activator is by an amidolytic assay. When human tissue-type plasminogen activator was added to whole blood in the presence of various concentrations of PPACK the human tissue-type plasminogen activator amidolytic activity was completely abolished with PPACK concentrations of 1 μM or greater (FIG. 1). The optical density of plasma with no added human tissue-type plasminogen activator was equal to the baseline optical density at 10 and 100 μM PPACK in plasma containing human tissue-type plasminogen activator.

2. Residual Thrombin Inhibitory Activity

Residual thrombin inhibitory activity can interfere with thrombin dependent fibrinogen assays unless it is determined that the thrombin added was still in excess. Residual thrombin inhibitory activity was determined by measuring the clotting time of plasma derived from whole blood collected with and without PPACK. FIG. 2 shows that the thrombin titration curves diverge when the thrombin concentration is below 7.5 U/ml; however, there is no significant difference between the two curves when the thrombin concentration is greater than 7.5 U/ml.

Since there is apparent residual PPACK activity in plasma, the PPACK concentration range was determined for blood samples which were to be used for fibrinogen determination by the thrombin dependent assay. FIG. 3 shows that, in the presence of 5 μg/ml human tissue-type plasminogen activator, there is complete in vitro loss of fibrinogen when the PPACK concentration is below 0.1 μM, due to continued activity of human tissue-type plasminogen activator. This in vitro plasminogen activation is eliminated at PPACK concentrations between 0.3 and 10 μM; however, when the PPACK concentration is greater than 10 μM there is a PPACK dependent inhibition of clotting either in the presence or absence of human tissue-type plasminogen activator.

Figure 4:
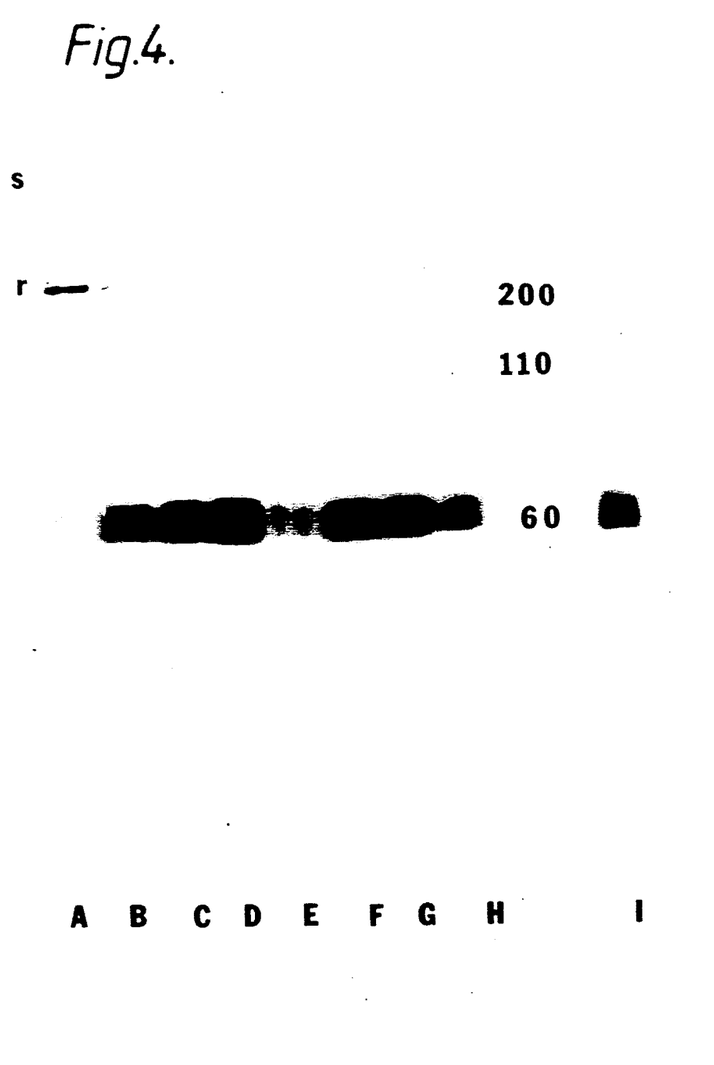
FIG. 4 is an autoradiogram of $^{125}$I human tissue-type plasminogen activator: A-D are human plasma, E-H are rabbit plasma, I is starting material. The concentrations of PPACK were 0, 0.5, 5, 50 $\mu$M respectively for A-D and E-H. The location of the top of the stacking gel and the running gel are indicated by (s) and (r), respectively.

3. Inhibition of Plasma Protease Inhibitor Human Tissue-type Plasminogen Activator Complex Formation The ability of PPACK to inhibit the formation of complexes of human tissue-type plasminogen activator with plasma protease inhibitors was determined in human and rabbit whole blood. PPACK was added at various concentrations to freshly drawn whole blood and human tissue-type plasminogen activator was added to a final concentration of 5 µg/ml and 4.5 µCi/ml. It is evident that human tissue-type plasminogen activator forms SDS-PAGE stable complexes resulting in species with apparent molecular weights of 110,000 and greater than 200,000 (FIG. 4). The formation of these complexes is maximally inhibited by PPACK at concentrations between 0.5 and 5 µM.

4. Comparison of PPACK and Aprotinin: In Vitro

Human and rabbit blood samples were collected either with aprotinin (200 KIU/ml) or PPACK (1.9 µM), spiked with human tissue-type plasminogen activator and the blood processing was deliberately delayed for 1 hour while the blood was held on ice, to simulate a delay which reasonably might be expected to occur in a clinical laboratory. Table 1 shows that both protease inhibitors blocked the consumption of fibrinogen. PPACK was clearly more effective when the Clauss assay was used and the two were equally effective when sodium sulfite precipitation method was used. The Bbeta 1-42 FDP results were the most significant demonstrating inhibition of human tissue-type plasminogen activator by PPACK in the in vitro formation of FDPs. As expected, the plasminogen and alpha-2-antiplasmin levels are greatly decreased by the presence of human tissue-type plasminogen activator; this effect is completely reversed by PPACK. The measurement of plasminogen and alpha-2-antiplasmin can be made with plasma which is prepared from whole blood containing up to 10 µM PPACK. It is important to note that it is not possible to measure these two parameters in the presence of aprotinin since it is a specific inhibitor of plasmin (25).

5. Comparison of Aprotinin and PPACK: In Vivo

Figure 5:
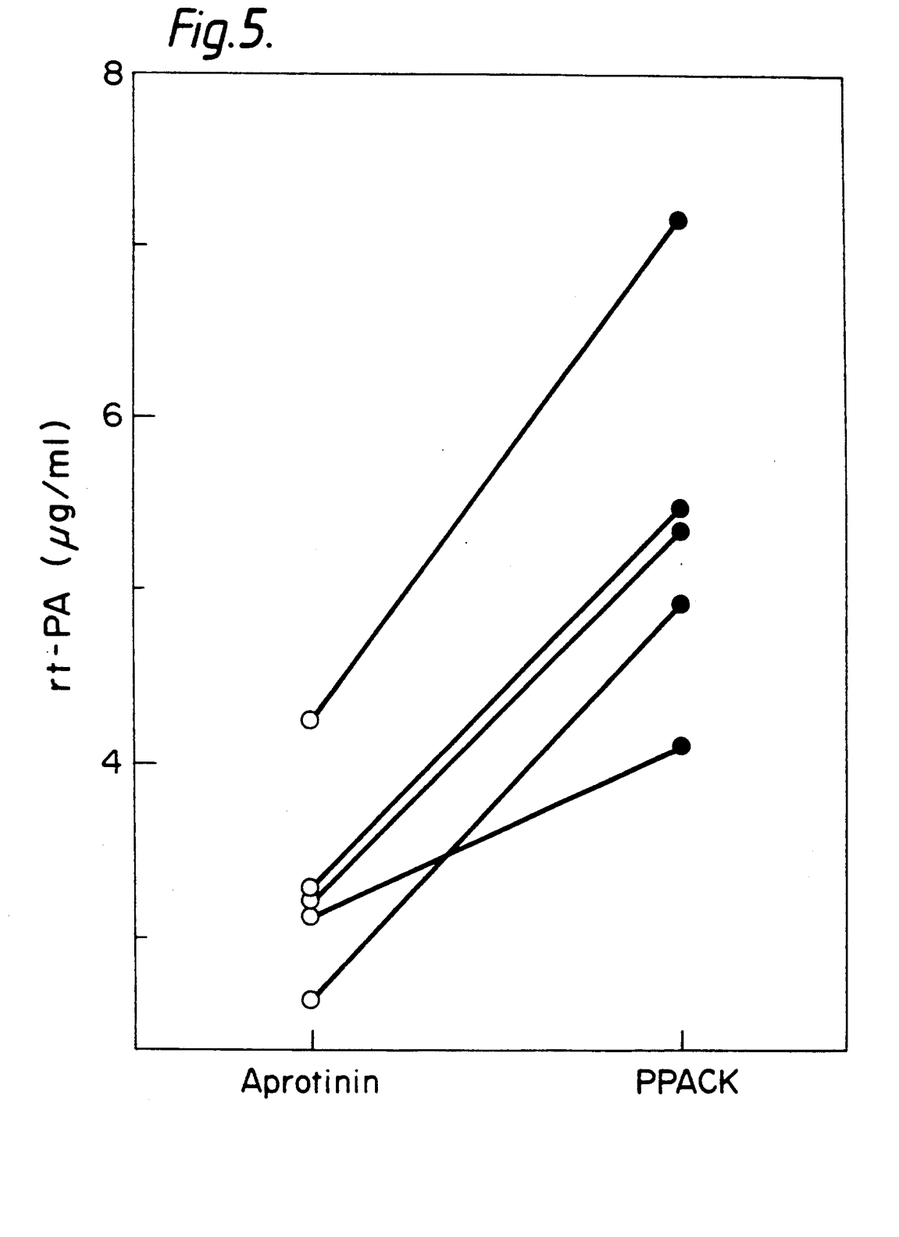
FIG. 5 shows a comparison to the effect of aprotinin (200 KIU/ml) and PPACK (1 µM) on the recovery of human tissue-type plasminogen activator immunoreactivity from Rhesus plasma. Samples were taken at 55 minutes during a 3 mg/kg/60 minute infusion.

Five Rhesus monkeys were given an infusion of human tissue-type plasminogen activator at 50 µg/kg/min over a 60 minute period and two independent blood samples were drawn at three times. One sample set collected with aprotinin and the other set was collected with 1 µM PPACK; both protease inhibitors were in the venipuncture syringe and the blood was rapidly chilled and processed. The individual immunoreactive human tissue-type plasminogen activator levels are shown in FIG. 5. There is a significant increase in the levels of immunoreactive human tissue-type plasminogen activator in the PPACK group (p<0.005 by a paired Student's T-test). Table 2 shows that at four hours, when very little human tissue-type plasminogen activator is present, fibrinogen levels in these animals decreased by about 20 percent measured by the Clauss assay and by 6 percent by the salt precipitation procedure. The 55 minutes samples, which contain substantial amounts of human tissue-type plasminogen activator, show similar changes. The samples which were collected on PPACK showed that there were decreases in plasminogen and alpha-2-antiplasmin that were indistinguishable at 55 minutes and 4 hours.

TABLE 1

|  | Fibrinogen Clauss (mg/ml) | Fibrinogen sulfite (mg/ml) | FDP pM/ml Bbeta 1-42 | Plasminogen (%/ml) | Alpha-2-Antiplasmin (%/ml) |
|---|---|---|---|---|---|
| Human | | | | | |
| Control | 2.64 ± 0.37 | 1.85 ± 0.01 | 3.40 ± 1.39 | 118 ± 8 | 130 ± 7 |
| t-PA[a, e] | 1.23 ± 0.01 | 0.92 ± 0.12 | 263 ± 20 | 20 ± 8 | 0.00[b] |
| t-PA + PPACK[a] | 3.35 ± 0.02 | 1.72 ± 0.07 | 11.62 ± 3.02 | 108 ± 6 | 130 ± 3 |
| t-PA + Aprotinin[a] | 1.99 ± 0.10 | 1.65 ± 0.05 | 157 ± 14 | c | c |
| Rabbit | | | | | |
| Control | 2.41 ± 0.16 | 1.50 ± 0.09 | d | 70 ± 2.5 | 163 ± 1 |
| t-PA | 0.70 ± 0.09 | 0.62 ± 0.01 | d | 18.2 ± 1.9 | 53.4 ± 3.4 |
| t-PA + PPACK | 2.13 ± 0.09 | 1.28 ± 0.07 | d | 80 ± 7 | 157 ± 7 |
| t-PA + Aprotinin | 1.65 ± 0.12 | 1.28 ± 0.09 | d | c | c |

Note: Values are mean ± s.d. (n = 3).
[a]Concentrations were: t-PA, 5 µg/ml; aprotinin, 200 KIU/ml, PPACK, 5 µM; for both human and rabbit.
[b]Residual plasmin activity.
[c]Aprotinin interferes with plasminogen and alpha-2-antiplasmin assays.
[d]Antibody apparently does not cross react with rabbit Bbeta 1-42.
[e]t-PA is recombinant human tissue-type plasminogen activator.

TABLE 2

| Treatment | Time[a] | Fibrinogen Clauss (mg/ml) | Fibrinogen Sulfite (mg/ml) | Plasminogen (%/ml) | Alpha-2-Antiplasmin (%/ml) |
|---|---|---|---|---|---|
| Aprotinin[b] | 0 | 1.94 ± 0.13 | 3.05 ± 0.51 | c | c |
|  | 55 min | 1.50 ± 0.13 | 2.10 ± 0.22 | c | c |
|  | 4 hr | 1.46 ± 0.29 | 2.86 ± 0.33 | c | c |
| PPACK[b] | 0 | 1.95 ± 0.40 | 2.96 ± 0.38 | 160 ± 24 | 135 ± 9 |
|  | 55 min | 1.74 ± 0.31 | 2.44 ± 0.24 | 75 ± 46 | 54 ± 7 |
|  | 4 hr | 1.57 ± 0.22 | 2.77 ± 0.20 | 109 ± 24 | 67 ± 11 |

Note: Values are mean ± s.d. (n = 5).
[a]Time after start of infusion.
[b]Concentrations were: aprotinin, 200 KIU/ml; PPACK, 1 µM.
[c]Aprotinin interferes with plasminogen and alpha-2-antiplasmin.

BIBLIOGRAPHY

1. Pennica et al., *Nature* 301, 214 (1983).

2. Collen, *Thromb. Haemos* 43, 77 (1980).
3. Bergmann et al., *Science* 220, 1181 (1983).
4. Walker et al., *Thromb. Haemostas* 47, 265 (1982).
5. Chmielewska et al., *Thromb. Res.* 31, 427 (1983).
6. Emeis, *Biochem. Biophys. Res. Comm.* 110; 392 (1983).
7. Haggroth et al., *Thrombosis Res.* 33, 583 (1984).
8. Coleman et al., *Biochim. et Biophy. Acta* 569, 41 (1979).
9. Lijnen et al., *Thromb. Res.* 34, 431 (1984).
10. Kettner et al., *Thromb. Res.* 14, 969 (1979).
11. Loskutoff, *Thromb. Haemos.* 54, 118 (1985).
12. Junan-Vague et al., *Thrombosis Res.* 33, 523 (1984).
13. Wiman et al., *Thromb. Haemos* 52, 124 (1984).
14. Friberger et al., *Progress in Chemical Fibrinolysis and Thrombolysis*, Vol. 4, Davidson, J. F. et al. (eds), Churchill Livingston, p. 149 (1979).
15. Rampling et al., *Clin. Chim Acta* 67, 43 (1976).
16. Vermylen et al., *Clin. Chim Acta* 8, 418 (1963).
17. Clauss, *Acta Haemat.* 17, 237 (1957).
18. Rijken et al., *J. Biol. Chem.* 257, 2920 (1982).
19. Laemmli, *Nature* 227, 680 (1970).
20. Kudryk, *Molecular Immunology* 20, 1191 (1983).
21. Friberger et al., *Haemostasis* 7, 138 (1978).
22. Friberger et al., *In Chromogenic Peptide Substrates*, Scully and Kakkar (eds.) Churchill Livingston, Edinburgh, Scotland, p. 128 (1979).
23. Alkjaersig, *Biochem. J.* 93, 171 (1964).
24. Edy et al., *Throm. Res.* 8, 513 (1976).
25. Steichele et al., *Med. Welt.* 42, 2170 (1961).

We claim:

1. A method for in vitro measurement of in vivo human tissue-type plasminogen activator from plasma comprising:
   contacting an aliquot of said plasma with D-Phe-Pro-Arg-Chlormethyl ketone in an amount sufficient to inhibit said human tissue-type plasminogen activator to a functionally inactive form and immunochemically quantitating said inactivated human tissue-type plasminogen activator.

2. A kit useful for assaying human tissue-type plasminogen activator comprising: (a) a container for receiving and housing a predetermined aliquot of plasma, said container containing D-Phe-Pro-Arg-Chlormethyl ketone in an amount sufficient to inhibit said human tissue-type plasminogen activator to a functionally inactive form, and (b) reagents functional to quantitate immunochemically said inactivated human tissue-type plasminogen activator in said predetermined aliquot of plasma.

3. A method of measuring the levels of both exogenous and endogenous human tissue-type plasminogen activator in a patient treated with said activator comprising:
   obtaining a first sample of the plasma of said patient,
   contacting an aliquot of said first plasma sample with D-Phe-Pro-Arg-Chloromethyl ketone in an amount sufficient to inhibit any endogenous human tissue-type plasminogen activator to a functionally inactive form.
   immunochemically quantitating said inactivated endogenous human tissue-type plasminogen activator in said first sample,
   administering to said patient exogenous human tissue-type plasminogen activator,
   obtaining a second sample of the plasma of said patient after administration of said exogenous human tissue-type plasminogen activator,
   contacting said second sample with D-Phe-Pro-Arg-Chlormethyl ketone in an amount sufficient to inhibit any human tissue-type plasminogen activator in said second sample to a functionally inactive form and
   immunochemically quantitating said inactivated human tissue-type plasminogen activator in said second sample to measure the levels of both exogenous and endogenous human tissue-type plasminogen activator in said patient.

* * * * *

UNITED STATES PATENT AND TRADEMARK OFFICE
CERTIFICATE OF CORRECTION

PATENT NO. : 5,096,811

DATED : March 17, 1992

INVENTOR(S) : HOTCHKISS, et al.

It is certified that error appears in the above-identified patent and that said Letters Patent is hereby corrected as shown below:

On the Title page, item (54), line 2, replace "Actuator"
with --Activator--.

Column 1, in line 2 of the title, replace "Actuator"
with --Activator--.

Signed and Sealed this

Eighth Day of June, 1993

Attest:

MICHAEL K. KIRK

Attesting Officer

Acting Commissioner of Patents and Trademarks